(12) United States Patent
Pan et al.

(10) Patent No.: US 9,215,981 B2
(45) Date of Patent: Dec. 22, 2015

(54) APPARATUS FOR ACQUIRING DATA OF TONGUE AND FACE IMAGES BASED ON TRADITIONAL CHINESE MEDICINE

(75) Inventors: Zhe Pan, Shangahi (CN); Huilin Zhou, Shanghai (CN); Yue Pan, Shanghai (CN); Yiqin Wang, Shangahi (CN)

(73) Assignee: SHANGHAI DAOSHENG MEDICAL TECHNOLOGY CO., LTD., Shanghai (CN)

( * ) Notice: Subject to any disclaimer, the term of this patent is extended or adjusted under 35 U.S.C. 154(b) by 825 days.

(21) Appl. No.: 13/143,643

(22) PCT Filed: May 10, 2010

(86) PCT No.: PCT/CN2010/000659
§ 371 (c)(1),
(2), (4) Date: Aug. 30, 2011

(87) PCT Pub. No.: WO2011/026305
PCT Pub. Date: Mar. 10, 2011

(65) Prior Publication Data
US 2011/0304718 A1    Dec. 15, 2011

(30) Foreign Application Priority Data

Sep. 1, 2009    (CN) .......................... 2009 1 0057861

(51) Int. Cl.
*H04N 7/18* (2006.01)
*A61B 5/00* (2006.01)
(Continued)

(52) U.S. Cl.
CPC ............. *A61B 5/0059* (2013.01); *A61B 5/0064* (2013.01); *A61B 5/4854* (2013.01);
(Continued)

(58) Field of Classification Search
CPC .... A61B 5/0059; A61B 5/0064; A61B 5/441; A61B 5/4854; A61B 5/682
See application file for complete search history.

(56) References Cited

U.S. PATENT DOCUMENTS 5,689,446 A * 11/1997 Sundman et al. ............. 702/167
6,861,269 B2 * 3/2005 Kawai et al. .................... 438/14
(Continued)

FOREIGN PATENT DOCUMENTS

| CN | 1387162 A | 12/2002 |
|---|---|---|
| CN | 2558014 | 6/2003 |

(Continued)

*Primary Examiner* — Dave Czekaj
*Assistant Examiner* — Md Haque
(74) *Attorney, Agent, or Firm* — Muncy, Geissler, Olds & Lowe, P.C.

(57) ABSTRACT

The present invention provides a device for collecting information from face and the tongue for Chinese medicine, which includes a tank, a light source and a shooting structure. The light source and the shooting structure are positioned inside the tank, the shooting structure contains a guide column, a lifting component, a shooting component and an electrical component. The guide column and the electrical component are fixed in the tank, the shooting component fixed on the lifting component, the lifting component fixed on the guide column, which can achieve adjustment of the relative to the guide column by the electrical component. The present invention also provides a method for collecting information collection from face and tongue for Chinese medicine, which includes: 1. collect the information of the face with the camera lens perpendicular to the face plane; 2. tilt forward the camera's position while raising to the vertical plane with the tongue, collect the further information of the tongue. The present invention can solve the disadvantage in the existing technology that the information collection from the tongue and face can not be achieved at the same time, and collecting process done automatically by the electric machine control, easy to operate.

8 Claims, 7 Drawing Sheets

(51) Int. Cl.
  *F16M 11/10*  (2006.01)
  *F16M 11/24*  (2006.01)
  *G03B 17/00*  (2006.01)
  *G03B 17/56*  (2006.01)

(52) U.S. Cl.
  CPC .............. *A61B 5/702* (2013.01); *F16M 11/10*
    (2013.01); *F16M 11/24* (2013.01); *G03B 17/00*
    (2013.01); *G03B 17/561* (2013.01); *A61B 5/441*
    (2013.01); *A61B 5/682* (2013.01)

(56) References Cited

U.S. PATENT DOCUMENTS

2002/0057360 A1\* 5/2002 Abe et al. ...................... 348/373

2006/0045485 A1\* 3/2006 Kawamura ...................... 386/95
2007/0141920 A1\* 6/2007 Mogamiya ...................... 439/752

FOREIGN PATENT DOCUMENTS

| CN | 1561904 | \* | 1/2005 |
| CN | 1561904 A | | 1/2005 |
| CN | 200994769 | \* | 12/2007 |
| CN | 200994769 Y | | 12/2007 |
| CN | 101202840 | | 6/2008 |
| CN | 201139551 Y | | 10/2008 |
| CN | 201481397 U | | 5/2010 |
| JP | 2004-235948 | | 8/2004 |

\* cited by examiner

APPARATUS FOR ACQUIRING DATA OF TONGUE AND FACE IMAGES BASED ON TRADITIONAL CHINESE MEDICINE

FIELD OF THE INVENTION

The invention relates to a detection and diagnosis device in Chinese medicine, specifically relates to a device for collecting the information from face and tongue. The invention also relates to a method for collecting the information based on the device mentioned above.

BACKGROUND OF THE INVENTION

The main sources of information of the traditional Chinese medicine diagnosis are the inspection, auscultation and olfaction, inquiry, and feeling the pulse, also known as "the four diagnosis". Wherein the inspection diagnosis mainly includes tongue diagnosis and face diagnosis and so on. The information gathered by traditional diagnosis largely relies on doctors' subjective qualitative observation and clinical experience, therefore there are unfavorable factors such as strong subjective dependence and poor reproducibility, and it's not easy to keep symptom records.

In order to achieve the objectification, the quantification and the standardization of inspection diagnosis of Chinese medicine, the sampling device with camera is used to take the image with information to detect the color, shape, texture and other characteristics of information to judge the state of the human body. Such as the Chinese Utility Model Patent ZL200720172978.1 (announced on Oct. 29, 2008) discloses a camera obscura for tongue image collection, which uses the confined space and the same position to ensure the quality of the color of the tongue which is acquired, but the details of the shooting structure is not described in the patent.

Structurally, the similar camera obscuras (shown in FIG. 1 and FIG. 2) currently usually includes tank 1, light source 2 and shooting structure 3, in most cases light source 2 and shooting structure 3 are positioned in the tank 1, and the shooting structure 3 is generally set fixed without auto focus function, so it can only achieve a unitary shot on face or tongue if this type camera obscuras is applied. In order to improve the accuracy of diagnosis, The TCM practitioners often need to consider the information shown both on face and on tongue, therefore, a device which will collect the information on face and tongue together needs to be developed.

DETAILED DESCRIPTION OF THE INVENTION

The technical problem needs to be solved by this invention is to provide a device for collecting information from face and tongue, which can collect the information from face and tongue respectively, and the collecting mode between the face and the tongue can be switched by the electric machine automatically. Therefore, this invention also provides a method to collect the information from face and tongue.

In order to solve the above-mentioned technical problem, this invention provide a device for collecting information from face and tongue, including a tank, a light source and a shooting structure. The light source and the shooting structure are positioned inside the tank, and the shooting structure contains a guide column, a lifting component, a shooting component and a electrical component. The guide column and the electrical component are fixed on the tank, the shooting component fixed in the lifting component, the lifting component fixed on the guide column, which can achieve the adjustment to the guide column by the electrical component.

Based on the above-mentioned device, the invention provides a method for collecting information from face and tongue for Chinese medicine, including the following steps:
(1) Collect the information of face with the camera lens perpendicular to the face plane;
(2) Further collect the information of the tongue with tilting forward the camera's position while raising to the vertical plane with the tongue.

With the device for collecting information collection from face and tongue of this invention, switching the collecting mode between the face and the tongue automatically can be achieved for the convenience of the integrated Chinese medicine diagnosis.

BRIEF DESCRIPTION OF THE DRAWINGS

Preferred embodiments of the present invention will now be more particularly described with reference to the accompanying drawings, wherein.

DETAILED DESCRIPTION OF PREFERRED EMBODIMENTS

Figure 1:
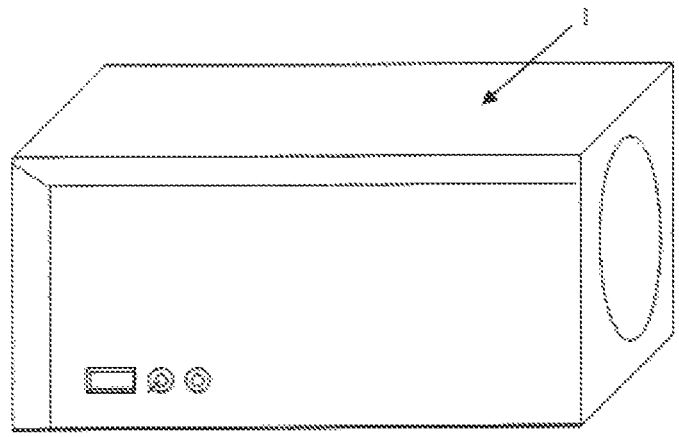
FIG. 1 is the appearance structure diagram of the existing device for the inspection diagnosis of Chinese medicine.
Figure 2:
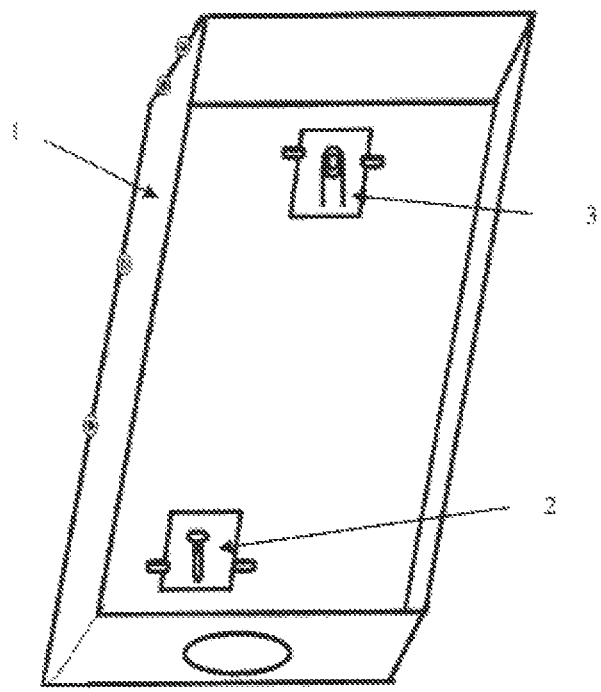
FIG. 2 is the internal structure diagram of the existing device for the inspection diagnosis of Chinese medicine.

As shown in FIG. 1 and FIG. 2, the traditional device for collecting information from face and tongue in Chinese medicine includes a tank 1, a light source 2 and a shooting structure 3, the light source 2 and the shooting structure 3 are positioned inside the tank 1. The invention mainly improves the design on the shooting structure 3 of the device, the shooting structure of the present invention can be fixed at the bottom of the tank, or put a circuit board box at the bottom of the tank, then fix the shooting structure on the upper surface of circuit board box.

Figure 3:
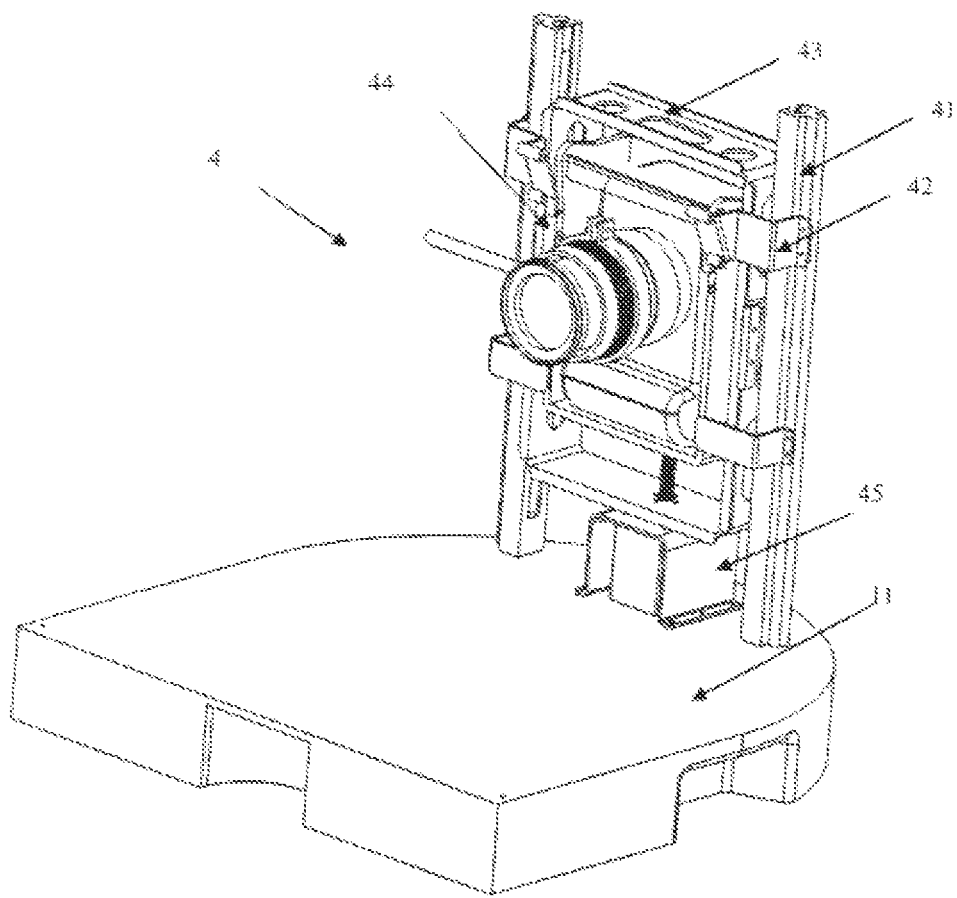
FIG. 3 is the block diagram of the shooting structure of the inspection diagnosis of Chinese medicine in the invention.

As shown in FIG. 3, the shooting component 4 of the present invention includes a guide column 41, a lifting component 43, a shooting component 44 and a electrical component 45. Guide column 41 and the electrical component 45 can be fixed on the bottom of the box directly or indirectly, preferably, on the upper surface of the circuit board box 11 at the bottom of the tank. The materials of the tank can be metal or non-metallic, so that the guide column 41 and electrical component 45 can be directly welded or fixed by screw. Shooting component 44 fixed in the lifting component 43, and the lifting component 43 mounted on guide column 41. Electrical component 45 is positioned below the lifting component 43 to raise or descend the lifting component 43.

Figure 5:
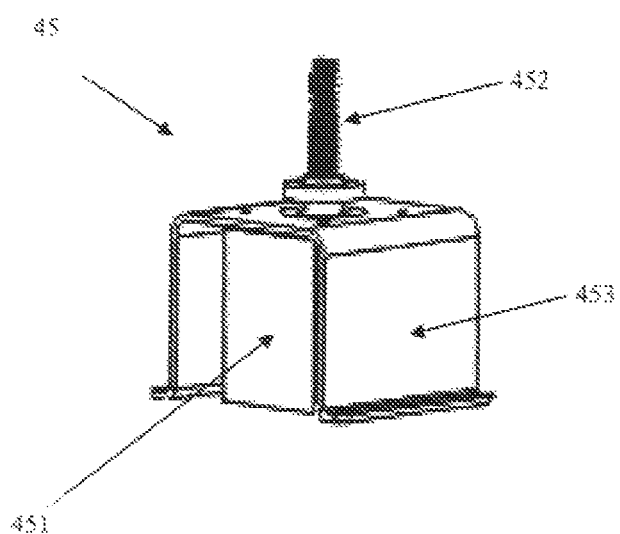
FIG. 5 is the block diagram of the electrical component of the shooting device in the invention.
Figure 6:
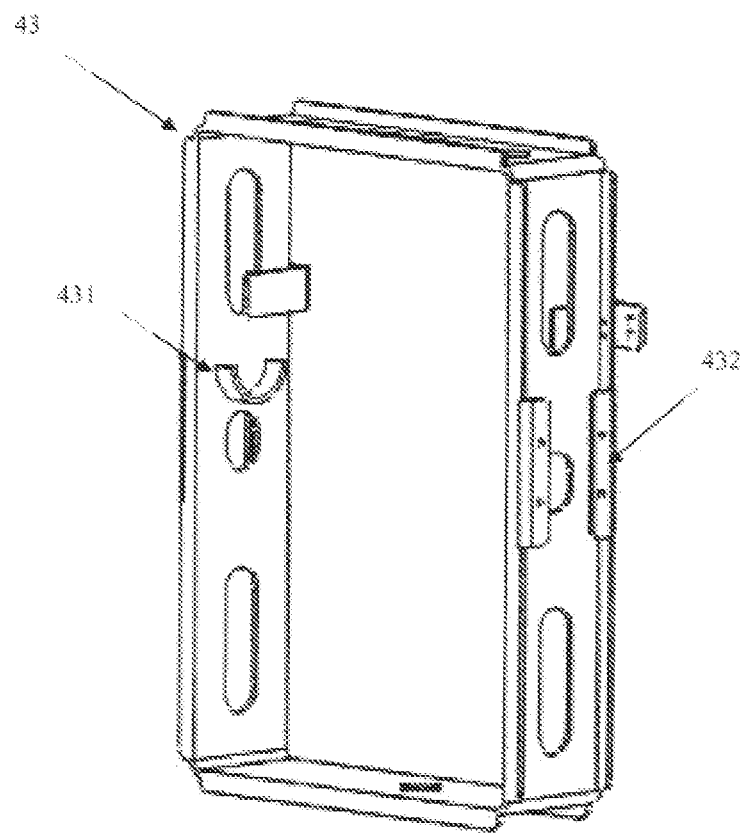
FIG. 6 is the block diagram of the lifting component of the shooting device in the invention.

As shown in FIG. 5, the electrical component 45 includes a motor 451 and a screw 452 which is connected with the motor 451, the top of screw 452 screws into the threaded hole in the bottom of the lifting component 43 (as shown in FIG. 6), and the motor 451 is fixed on the circuit board box by the motor seat 452. The motor 451 is used to control screw 452 clockwise or counterclockwise rotation, then drive the lifting component 43 up or down along the guide column 41 to meet the height adjustment of the camera while shooting the face and the tongue.

Figure 4:
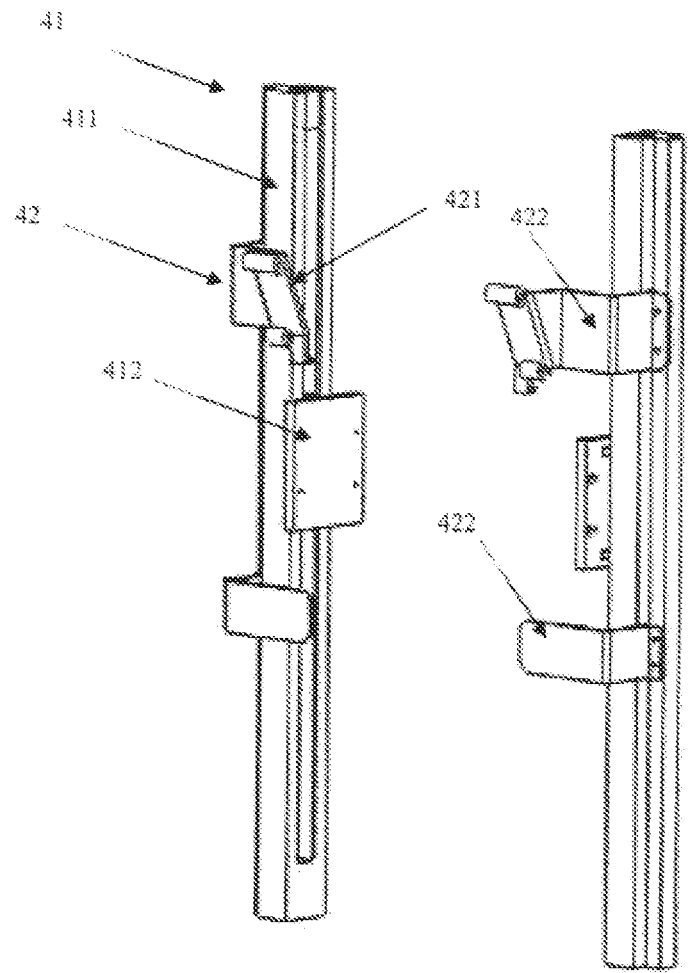
FIG. 4 is the block diagram of the guide column of the shooting device in the invention.

As shown in FIG. 4, more than 2 angle guide pieces 42 are fixed on the guide column 41 (there are four in the figure), the angle guide piece 42 which is located in the up side with the inclined plane 421 to guide the camera to tilt forward while raising, the angle guide piece 42 which is located in the lower with the vertically plane 422 to guide the camera to lift steadily. When the electrical component 45 leads the lifting component 43 to rise, the camera raising steadily with the vertical guide plane 422, while the camera has a lens which can protract, whose center of gravity is toward the front, so under the guidance of the inclined plane 421 with the angle of guide piece 42 the camera can tilt forward, the angle of the tilted camera is identical with the angle of the inclined plane 421, and the angle ranges between 10° and 30°.

Preferably, guide columns 41 are a pair of slotted metal rods 411 facing against each other with slot, their respective opposite sides of the metal rod contain the longitudinal extension of the slot, the slot may partly extend the metal rod or extend the both ends of the metal rod, a slider 412 is positioned on the metal rod 411, the slider 412 can slide in the slot, the slider 412 permanently connect to the connecting part of two laterals 432 of lifting component 43 (as shown in FIG. 6), which can be riveted or screw fixation, so that the lifting component 43 and the shooting component 44 can slide on the guide column 41.

Figure 7:
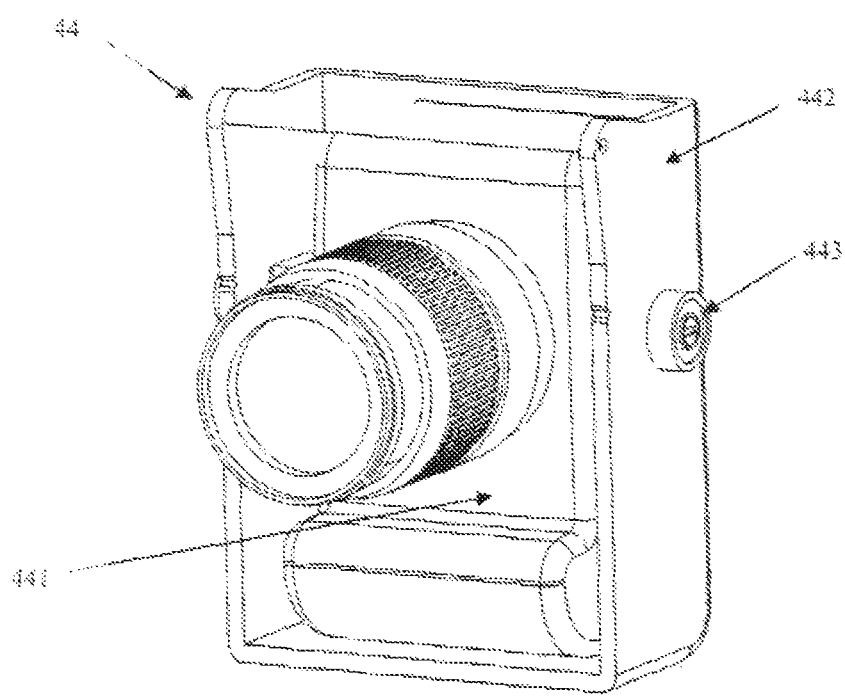
FIG. 7 is the three-dimensional diagram of the shooting component of the shooting device in the invention.

Further, as shown in FIG. 6, the connecting part of two laterals 432 outside the lifting component fix with the slider 412, both of the medial sides of the lifting component contain flake-like parts of semicircular arc 431, and the flake-like parts are fixed by welding. As shown in FIG. 7, the shooting component 44 includes a camera 441 and a camera container 442, the two laterals of the camera container 442 carries a pair of rotatable bearings 443, the pair of the bearings 443 are set on the flake-like parts 431 assemble on the inner side of the lifting component 43, the camera container 442 can rotate an angle in the lifting component 43.

The steps of the invention of the device for collecting information from face and tongue includes two steps: collect the face information and the tongue information. When shooting the face, the camera's lens plane perpendicular to the face and collect the information from the face; when shooting the tongue, tilt forward while raising the camera position to the vertical plane with the tongue, and collect the further information from tongue. Switching process in details are as follows:

When needs to switch from shooting the face to shoot the tongue, the screw 452 of the electrical component 45 rotates clockwise, so that the shooting component 44 can be raised, and the shooting component 44 moves upward along the angle guide pieces 42 of the vertical guide plane 442, since the weight of the front lens of the camera, the center of gravity is out of the lifting component, the component have taken the trend of outward tilting. When the shooting component 44 rises further, the weight of the camera forces the rotating bearing 443 to rotate, it turns outward and against the angle guide piece 42 which on the upside of the metal rod 411 of the inclined plane 421, so when the camera tilts, the angle is as same as the angle of the inclined plane 421, and the angle ranges between 10°-30°. In this way, the switch from shooting the face to shoot the tongue can be achieved.

Figure 8:
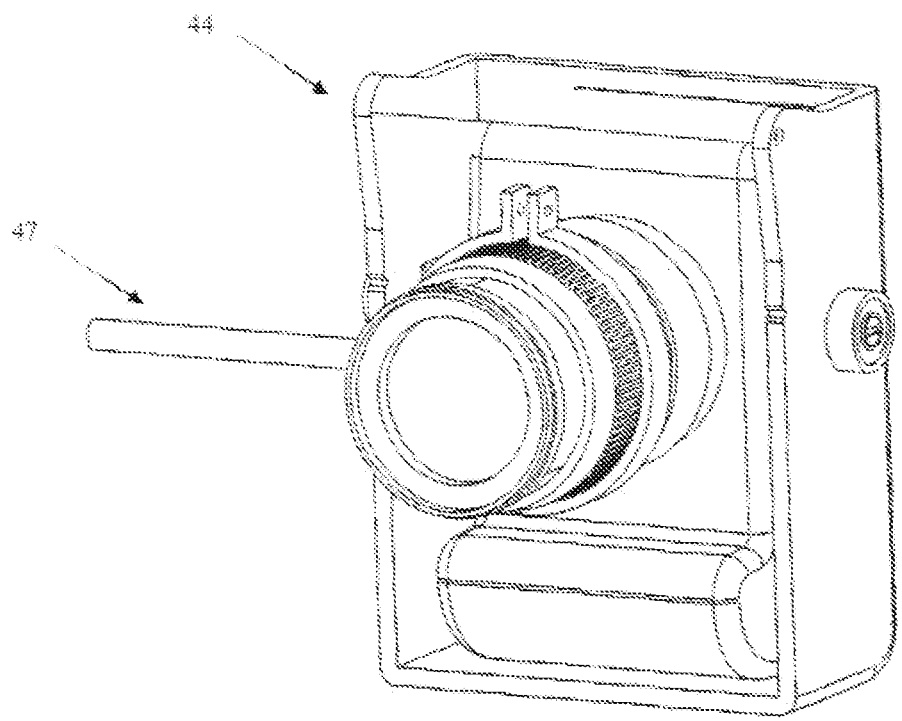
FIG. 8 is the schematic diagram of the shooting component with a rotating handle in the invention.

Preferably, when the camera's position changes from perpendicular to the face to perpendicular to the tongue, little change of distance between the lens and the film surface occurred, the present invention provides a mechanical structure that can automatically rotate the camera's lens to focus. As shown in FIG. 8, the shooting component 44 of the invention also contains an angle rotary handle 47, one end of the angle rotary handle 47 surrounds the camera lens 441 and can rotate the lens and the other end of the angle rotary handle 47 fixed on the tank 1 or adopt the fixation which can keep the angle rotary handle 47 and the tank 1 relatively static, so that when the camera rises, one end of the angle rotary handle 47 fixed, the other end can rotate the lens to achieve to focus tongue shot, when the camera descends, it can be reversed to the original location. Since the structural features of different cameras, the angle required to change respectively while adjusting the focal length, the optimal angle range is 0°-40°.

We can pre-set up the relation between the raising distance of the shooting component and the angle of the lens which controlled by the angle rotating handle, so that when the camera lens rotates down at any angle, the lens focal length can be sure to focus.

Similarly, when needs to switch from shooting the tongue to shoot the face, the screw 452 of the electrical component 45 rotates counter-clockwise, consequently the shooting component 44 descends and the shooting component 44 moves downward the vertical guide plane 442 along the angle guide pieces 42. This process is reverse to the raise process, and the angle ranges between 10°-30°. In this way, the switch from shooting the tongue to shoot the face can be achieved.

According to the preferred embodiment, a device for collecting information from face and tongue which is absence in the existing technology can be provided, which is able to achieve the information collection from the patient's tongue and face at one-time. It is beneficial to integrated analysis and comprehensive judge for the patients' focus.

The invention claimed is:

1. A device for collecting information from a face and a tongue for Chinese medicine, the device comprising:
   a tank, a light source and a shooting structure, and the light source and the shooting structure are positioned in the tank, and the shooting structure comprises:
   two vertically arranged guide columns;
   a lifting component which includes an electrical component and a frame, the frame being slidably coupled to the two guide columns and movable along the two guide columns driven by the electrical component;
   a shooting component arranged in the frame and rotatable with respect to the frame around an axis perpendicular to the two guide columns;
   a first pair of guide pieces fixed on the two guide columns at a first height, wherein the first pair of guide pieces are configured to guide the shooting component to move along the two guide columns in a substantially vertical direction before the shooting component is raised to a preset height; and
   a second pair of guide pieces fixed on the two guide columns at a second height higher than the first height, wherein each of the second pair of guide pieces includes an inclined plane and is configured to support the shooting component with the inclined plane upon the shooting component is raised to the preset height and rotates forward with respect to the frame.

2. The device of claim 1, wherein an angle of the inclined plane ranges between 10°-30°.

3. The device of claim 1, wherein the two guide columns are two metal rods positioned opposite to each other, and each of the two metal rods has a vertical slot formed therein and further includes a slider slidable in the vertical slot, and the slider for each metal rod is connected to the frame of the lifting component.

4. The device of claim 1, wherein the electrical component is connected to a bottom of the frame of the lifting component with a screw, the screw can raise and lower the frame by forward rotation and reverse rotation.

5. The device of claim 4, wherein the electrical component contains an electric machine to control the screw to rotate forward and reverse.

6. The device of claim 1, wherein the lifting component further includes a pair of concave plates each having a shape of a semicircular arc disposed on inner side faces of the frame; the shooting component includes a pair of bearings, a camera and a camera container; the camera is fixed in the camera container and the pair of bearings are disposed on outer side faces of the camera container and received in the pair of concave plates such that the camera container and the camera are rotatable with respect to the frame.

7. The device of claim 6, wherein the shooting component further contains an angle rotary handle, one end of which surrounds a rotatable lens of the camera, the other end of which is fixed on the tank to keep the angle rotary handle and the tank relatively static, so that the lens can rotate while the camera is raised or lowered.

8. The device of claim 7, wherein a rotation angle of the lens while the camera is raised or lowered is 0°-40°.

* * * * *